(12) United States Patent
Yang (10) Patent No.: US 10,537,254 B2
(45) Date of Patent: Jan. 21, 2020

(54) BLOOD PRESSURE CALCULATION METHOD BASED ON PULSE RETURN WAVE TRANSMISSION TIME, AND BLOOD PRESSURE MONITOR

(71) Applicant: HANGZHOU NANOCHAP ELECTRONICS CO., LTD., Zhejiang (CN)

(72) Inventor: Jiawei Yang, Zhejiang (CN)

(73) Assignee: HANGZHOU NANOCHAP ELECTRONICS CO., LTD., Zhejiang (CN)

( * ) Notice: Subject to any disclaimer, the term of this patent is extended or adjusted under 35 U.S.C. 154(b) by 184 days.

(21) Appl. No.: 15/562,253

(22) PCT Filed: Apr. 20, 2016

(86) PCT No.: PCT/CN2016/079694
§ 371 (c)(1),
(2) Date: Sep. 27, 2017

(87) PCT Pub. No.: WO2017/016245
PCT Pub. Date: Feb. 2, 2017

(65) Prior Publication Data
US 2018/0078157 A1    Mar. 22, 2018

(30) Foreign Application Priority Data
Jul. 28, 2015   (CN) .......................... 2015 1 0447025

(51) Int. Cl.
*A61B 5/021*     (2006.01)
*A61B 5/024*     (2006.01)
(Continued)

(52) U.S. Cl.
CPC .......... *A61B 5/02125* (2013.01); *A61B 5/022* (2013.01); *A61B 5/02438* (2013.01);
(Continued)

(58) Field of Classification Search
CPC . A61B 5/02125; A61B 5/022; A61B 5/02438; A61B 5/6826; A61B 5/7225; A61B 5/7246; A61B 5/7278; A61B 5/742
(Continued)

(56) References Cited

U.S. PATENT DOCUMENTS 6,554,763 B1 * 4/2003 Amano ................. A61M 21/00
                                                  600/26
2003/0036685 A1   2/2003 Goodman
(Continued)

FOREIGN PATENT DOCUMENTS

CN          1175892       3/1998
CN        102223837      10/2011
(Continued)

OTHER PUBLICATIONS

Theodor et al., "Implantable accelerometer system for the determination of blood pressure using reflected wave transit time", Sensors and Actuators A, No. 206, Dec. 14, 2013, pp. 151-158, ISSN: 0924-4247 (p. 1, right-hand column to p. 2, right-hand column, paragraph 2, and figure 1).
(Continued)

*Primary Examiner* — Daniel L Cerioni
(74) *Attorney, Agent, or Firm* — Greenblum & Bernstein, P.L.C.

(57) ABSTRACT

A method for calculating blood pressure based on pulse return wave transmission time, and a blood pressure monitor have been provided. The method includes the following steps: S1: collecting and storing pulse waveform data at a fingertip; S2: processing said pulse waveform data to obtain a heart rate and parameters of a plurality of pulse periods, detecting time axis coordinates of a primary wave starting point SPL1 of a pulse wave and a growth point SPL2 of a return wave in each of said pulse periods, and calculating a
(Continued)

corresponding pulse return wave transmission time RWTT: RWTT=SPL2−SPL1; S3: calculating the pulse return wave transmission time RWTT in each of said pulse periods to form a RWTT array; and S4: calculating systolic and diastolic pressures based on said RWTT array and the heart rate.

20 Claims, 5 Drawing Sheets

(51) Int. Cl.
    *A61B 5/022*     (2006.01)
    *A61B 5/00*     (2006.01)

(52) U.S. Cl.
    CPC .......... *A61B 5/6826* (2013.01); *A61B 5/7225* (2013.01); *A61B 5/7246* (2013.01); *A61B 5/7278* (2013.01); *A61B 5/742* (2013.01); *A61B 2560/0214* (2013.01); *A61B 2560/0475* (2013.01)

(58) Field of Classification Search
    USPC ........................................................ 600/485
    See application file for complete search history.

(56) References Cited

U.S. PATENT DOCUMENTS

| | | | |
|---|---|---|---|
| 2007/0016085 | A1 | 1/2007 | Inukai et al. |
| 2007/0149870 | A1* | 6/2007 | Rosenthal .......... A61B 5/02405 600/323 |
| 2012/0172734 | A1 | 7/2012 | Fujii et al. |
| 2014/0288445 | A1 | 9/2014 | Makkonen et al. |
| 2014/0323876 | A1 | 10/2014 | McGonigle et al. |
| 2015/0112172 | A1* | 4/2015 | Atlee .................. A61B 5/1459 600/325 |

FOREIGN PATENT DOCUMENTS

| | | |
|---|---|---|
| CN | 102258365 | 11/2011 |
| CN | 102688024 | 9/2012 |
| CN | 103260503 | 8/2013 |
| CN | 103393415 | 11/2013 |
| CN | 203815441 | 9/2014 |
| CN | 105054918 | 11/2015 |
| CN | 204813858 | 12/2015 |
| EP | 0818175 | 1/1998 |

OTHER PUBLICATIONS

Fung et al., "Continuous Noninvasive Blood Pressure Measurement by Pulse Transit Time", Proceedings of the 26th Annual International Conference of the IEEE EMBS, Sep. 1-5, 2004, pp. 738-741.

Fukushima et al., "Cuffless Blood Pressure Estmation using only Photoplethysmography based on Cardiovascular parameters", 35th Annual International Conference of the IEEE EMBS, Jul. 3-7, 2013, pp. 2132-2135.

Poon et al., "Cuff-less and Noninvasive Measurements of Arterial Blood Pressure", Proceedings of the 2005 IEEE Engineering in Medicine and Biology 27th Annual Conference, Sep. 1-4, 2005, pp. 5877-5880.

Cattivelli et al., "Noninvasive Cuffless Estimation of Blood Pressure from Pulse Arrival Time and Heart Rate with Adaptive Calibration", 2009 Body Sensor Networks, 2009, pp. 114-119.

Suzuki et al., "Cuffless and Non-invasive Systolic Blood Pressure Estimation for Aged Class by Using a Photoplethysmograph", 30th Annual International IEEE EMBS Conference, Aug. 20-24, 2008, pp. 1327-1330.

Gu et al., "A Novel Parameter from PPG Dicrotic Notch for Estimation of Systolic Blood Pressure Using Pulse Transit Time", Proceedings of the 5th International Workshop on Wearable and Implantable Body Sensor Networks, in conjunction with the 5th International Summer School and Symposium on Medical Devices and Biosensors, Jun. 1-3, 2008, pp. 86-88.

Millasseau et al., "Contour analysis of the photoplethysmographic pulse measured at the finger", Journal of Hypertension, 2006, vol. 24, Nov. 8, 2006, pp. 1449-1456.

Search Report issued in International Patent Application No. PCT/CN2016/079694, dated Jun. 28, 2016.

Office Action issued in China Counterpart Patent Appl. No. 201510447025.0, dated Apr. 20, 2017.

Stefano Omboni et al.: "Evaluation of 24-Hour Arterial Stiffness Indices and Central Hemodynamics in Healthy Normotensive Subjects versus Treated or Untreated Hypertensive Patients: A Feasibility Study" International Journal of Hypertention, vol. 2015 (Jan. 2015).

Michael Theodor et al.: "Implantable Acceleration Plethysmography for Blood Pressure Determination," Conference proceedings: 35th Annual International Conference of the IEEE Engineering in Medicine and Biology Society (Jul. 2013).

Ruiping Wang et al.: "Cuff-Free Blood Pressure Estimation Using Pulse Transit Time and Heart Rate" Proceedings: 12th International Conference on Signal Processing (Oct. 2014).

Anirban Dutta Choudhury et al.: "Estimating Blood Pressure using Windkessel Model on Photoplethysmogram," Conference Proceedings: 36th Annual International Conference of the IEEE Engineering in Medicine and Biology Society (Aug. 2014).

Ramakrishna Mukkamala et al.: "Toward Ubiquitous Blood Pressure Monitoring via Pulse Transit Time: Theory and Practice," IEEE Transactions on bio-medical engineering, vol. 62, No. 8 (Aug. 2015).

Aishwarya Visvanathan et al.: "Estimation of Blood Pressure levels from Reflective Photoplethysmograph using Smart Phones," 13th IEEE International Conference on BioInformatics and BioEngineering (Nov. 2013).

* cited by examiner

FIG. 5

BLOOD PRESSURE CALCULATION METHOD BASED ON PULSE RETURN WAVE TRANSMISSION TIME, AND BLOOD PRESSURE MONITOR

TECHNICAL FIELD

The present disclosure relates to a blood pressure calculation method based on pulse return wave transmission time and a blood pressure monitor, and belongs to the technical field of medical device.

RELATED ART

All of the conventional electronic blood pressure monitors must perform pressurizing and depressurizing through a cuff, and measure the blood pressure by auscultation or oscillography. Due to the discomfort caused by the pressurization of the cuff, this type of blood pressure monitor is called an invasive blood pressure monitor. In recent years, there have been some non-invasive blood pressure monitors, which calculate the pulse wave propagation velocity generally based on the measured pulse wave transmission time (PTT) and PTT-BP blood pressure model, and further estimate the systolic pressure.

As disclosed in Chinese Patent Announcement No. CN102223837B, entitled "Blood Pressure Information Measuring Device for Measuring Pulse Wave Velocity as Blood Pressure Information", in a measuring device, cuffs which are worn respectively at the upper arm and the lower limb (ankle) are used to measure the blood pressure of the upper arm and the blood pressure of the lower limb (S101). Further, the pulse wave of the upper arm and the pulse wave of the lower limb are measured synchronously by using these cuffs (S103). Then, the pulse wave propagation velocity (baPWV) at the upper arm and the lower limb is calculated based on the difference of the occurrence time between the two pulse waves (S105, S107). Further, the upper arm pulse wave propagation velocity (upper arm PWV) is calculated based on the difference of the occurrence time between the ejection wave and the return wave of the upper arm pulse wave (S109, S111). This method requires two sensors, generally, one placed in the vicinity of the heart for receiving the heart sound signal (ECG), and the other placed at the human limbs (wrist, fingers, foot, etc.) or behind the ears and other parts for receiving the pulse wave signal (usually obtained by photoplethysmography, i.e., PPG) propagated thereto. By comparing the two signals, the pulse wave transmission time is measured. In this method, the two sensors each have a corresponding circuit and are connected to each other by a wire, so that they are not convenient to use and are usually incorporated into some wearable garments (accessories). There are also ways to place two sensors directly at the wrist and fingers, thereby measuring the PTT from the wrist to the fingers by comparing the pulse wave signal thereat. However, the pulse wave velocity calculated by this method is local and does not conform to the definition in the PTT-BP blood pressure model, so that the estimated systolic pressure value will have a relatively large deviation.

SUMMARY

The technical problem to be solved by the present disclosure is to provide a new blood pressure electronic measurement technique and method based on the return wave transmission time (RWTT) in order to alleviate at least one of the above deficiencies. In the new technique and method, only one sensor is required, and by touching the sensor with fingers, the diastolic pressure, systolic pressure, heart rate and other values could be calculated through complex algorithms in just a few seconds.

The technical solution for solving the technical problem of the disclosure is as follows:

A method for calculating blood pressure based on pulse return wave transmission time, comprising steps of:

S1: collecting and storing pulse waveform data at a fingertip;

S2: processing said pulse waveform data to obtain a heart rate and parameters of a plurality of pulse periods, detecting time axis coordinates of a primary wave starting point SPL1 of a pulse wave and a growth point SPL2 of a return wave in each of said pulse periods, and calculating a corresponding pulse return wave transmission time RWTT: RWTT=SPL2−SPL1;

S3: calculating the pulse return wave transmission time RWTT in each of said pulse periods to form a RWTT array; and S4: calculating systolic and diastolic pressures based on said RWTT array and the heart rate.

Preferably, the method further comprises a step S5 of correcting the calculated systolic and diastolic pressures for each individual.

Preferably, the method further comprises a step S21 of correcting said growth point SPL2 of the return wave in accordance with profile characteristics of different types of pulse waves.

Preferably, the step of calculating the systolic pressure comprises establishing a systolic pressure SYS formula according to said RWTT array $$SYS = K_s \cdot 266 \cdot \frac{height^2}{RWTT^2},$$

where $K_S$ is 1.2-1.8, preferably 1.5.

Preferably, the step of calculating the diastolic pressure comprises establishing a first diastolic blood pressure DIA formula according to said RWTT array $$DIA = \frac{K_{d1}}{RWTT^2} + K_{d2} \cdot HR,$$

wherein $K_{d1}$ is 2.1-3.3, preferably 2.7, $K_{d2}$ is 0.3-0.8, preferably 0.5, and HR is the heart rate.

Preferably, the step of calculating the diastolic pressure comprises establishing a second diastolic blood pressure DIA formula according to said RWTT array $$DIA = \frac{K_{d1}}{RWTT^2} + \frac{K_{d2}}{T_d} + \frac{K_{d3}}{SL},$$

where $K_{d1}$ is 1.6-2.4, preferably 2, $K_{d2}$ is 12-18, preferably 15, $K_{d3}$ is 52 ($P_{nor}$-DC) to 79 ($P_{nor}$-DC), preferably 66 ($P_{nor}$-DC), SL is a normalized slope, and $P_{nor}$ and DC are reference peak and reference DC voltage in the pulse period, respectively.

Preferably, the step S5 comprises: comparing the calculated systolic and diastolic pressures with predetermined standard values, and obtaining a systolic pressure correction parameter $K_{sc}$ and a diastolic pressure correction parameter $k_{dc}$; and substituting the systolic pressure correction parameter $K_{sc}$ into the systolic pressure SYS formula to form a corrected systolic pressure SYS formula, and substituting the diastolic pressure correction parameter $K_{dc}$ into the first diastolic pressure DIA formula and second diastolic pressure DIA formula, respectively, to form a corrected first diastolic pressure DIA formula and a corrected second diastolic pressure DIA formula.

Preferably, the corrected systolic pressure SYS formula is $$SYS = K_s \cdot 266 \cdot \frac{height^2}{RWTT^2} \cdot K_{sc},$$

where $K_S$ is 1.2-1.8, preferably 1.5.

Preferably, the corrected first diastolic blood pressure DIA formula is $$DIA = \frac{K_{d1}}{RWTT^2} + K_{d2} \cdot HR + K_{dc},$$

where $K_{d1}$ is 2.1-3.3, preferably 2.7, $K_{d2}$ is 0.3-0.8, preferably 0.5, and HR is the heart rate.

Preferably, the corrected second diastolic blood pressure DIA formula is $$DIA = \frac{K_{d1}}{RWTT^2} + \frac{K_{d2}}{T_d} + \frac{K_{d3}}{SL} + K_{dc},$$

where $K_{d1}$ is 1.6-2.4, preferably 2, $K_{d2}$ is 12-18, preferably 15, $K_{d3}$ is 52 ($P_{nor}$-DC) to 79 ($P_{nor}$-DC), preferably 66 ($P_{nor}$-DC), and SL is a normalized slope.

Preferably, instead of said RWTT array, a median RTM of the calculated RWTT array for all of the pulse periods collected in 10 seconds is used to calculate medians of systolic and diastolic pressures over 10 seconds.

Preferably, medians or averages of the calculated heart rate HR and normalized slope SL for all of the pulse periods collected in 10 seconds are used as said heart rate HR and said normalized slope SL.

A blood pressure monitor employing the above blood pressure calculation method based on a pulse return wave transmission time, comprising a pulse sensor, wherein the pulse sensor is connected in turn with a linear current-to-voltage conversion circuit, a unity gain buffer, a low-pass amplifier circuit, an analog-to-digital conversion circuit, and a processor, and the processor is further connected with a power supply.

Preferably, only one said pulse sensor is provided.

Preferably, said processor is further connected with a memory and/or a display and input module and/or a low dropout linear regulator.

Preferably, the low-pass amplifier circuit has a cutoff frequency of 20-50 Hz.

Preferably, the analog-to-digital conversion circuit has its sampling rate set to 1 kS/s.

Preferably, the processor performs low pass digital filtering on digitized data with a cutoff frequency of 10 Hz to further remove the noise.

The disclosure has the advantages that:

(1) the blood pressure calculation method of the disclosure uses only one sensor to measure the fingertip pulse, thus achieving simplicity, convenience, and quickness. By analyzing a corresponding theory basis of a pulse return wave and a human blood pressure, correlation models between RWTT and a systolic pressure as well as a diastolic pressure are established, and the systolic pressure and the diastolic pressure are calculated according to two blood models. The systolic pressure and the diastolic pressure, calculated by means of the present method, have higher accuracy, less error, and broad range of application. At the same time, the disclosure combines the technique with the PPG pulse sensor, obtains the pulse waveform by fingers contacting the pulse sensor and carries on a series of analysis and calculation for the pulse waveform, finally calculates the blood pressure and obtains the heart rate data.

(2) The second diastolic pressure DIA formula of the present disclosure has added a parameter of normalized slope in consideration of the influence of the normalized slope, and thus is more suitable for those who have abnormal attenuation rates during blood pressure diastole, and the measured diastolic pressure is more accurate.

(3) The present disclosure corrects the calculated systolic and diastolic pressures for each individual. When a user uses the electronic product of the present disclosure, it is necessary to input the height and measurement data with standard mercury sphygmomanometer. By using individual height value and performing individual automatic blood pressure correction, more accurate measurement results may be obtained for different patients.

BRIEF DESCRIPTION OF THE DRAWINGS

The disclosure will now be further described with reference to the accompanying drawings and embodiments.

REFERENCE NUMERALS

1—pulse wave sensor, 2—linear current-to-voltage conversion circuit, 3—unity gain buffer, 4—low-pass amplifier circuit, 5—analog-to-digital conversion circuit, 6—processor, 7—internal memory, 8—external memory, 9—display and input module, 10—power supply, 11—low dropout linear regulator.

DETAILED DESCRIPTION

The present disclosure will now be described in further detail with reference to the accompanying drawings. All of the drawings are simplified schematic diagrams, and depict the basic structure of the present disclosure by way of illustration only, and therefore only show the configurations related to the present disclosure.

Embodiment 1

Figure 1:
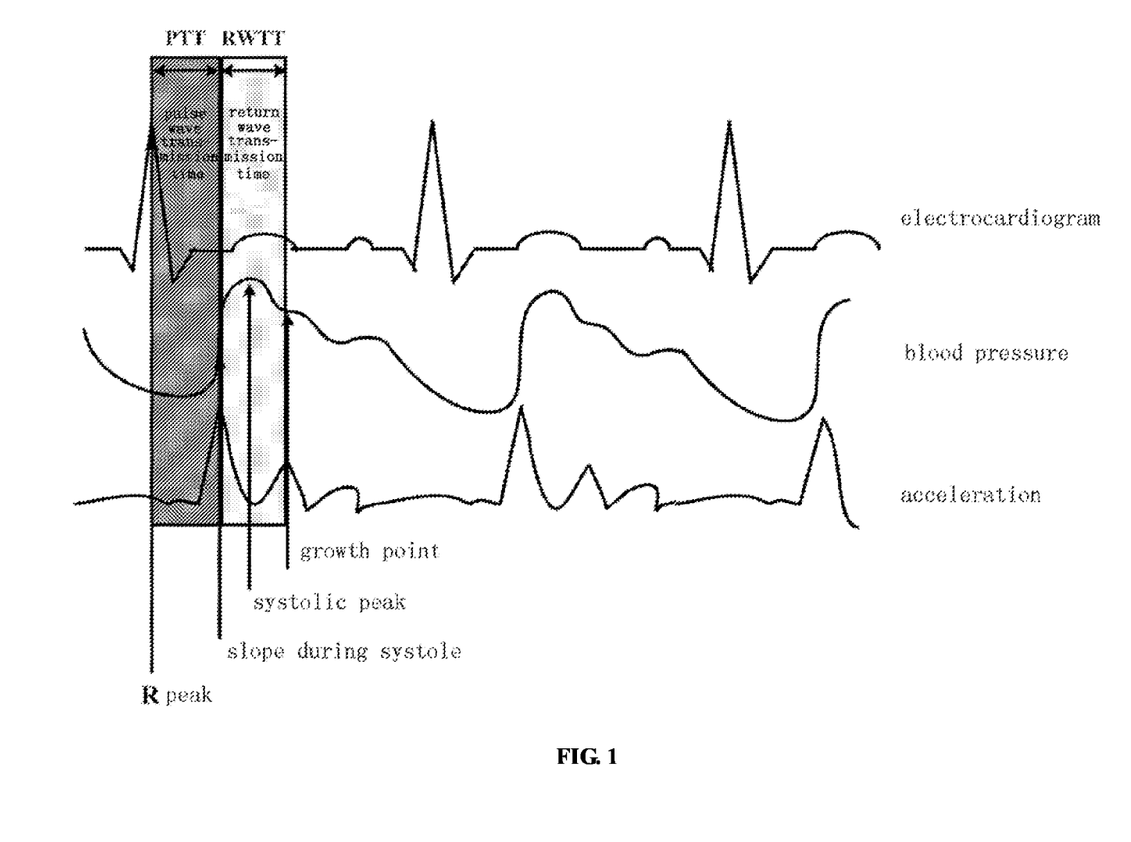
FIG. 1 is a graph showing a relationship between a pulse return wave transmission time (RWTT) and a pulse wave transmission time (PTT)
Figure 2:
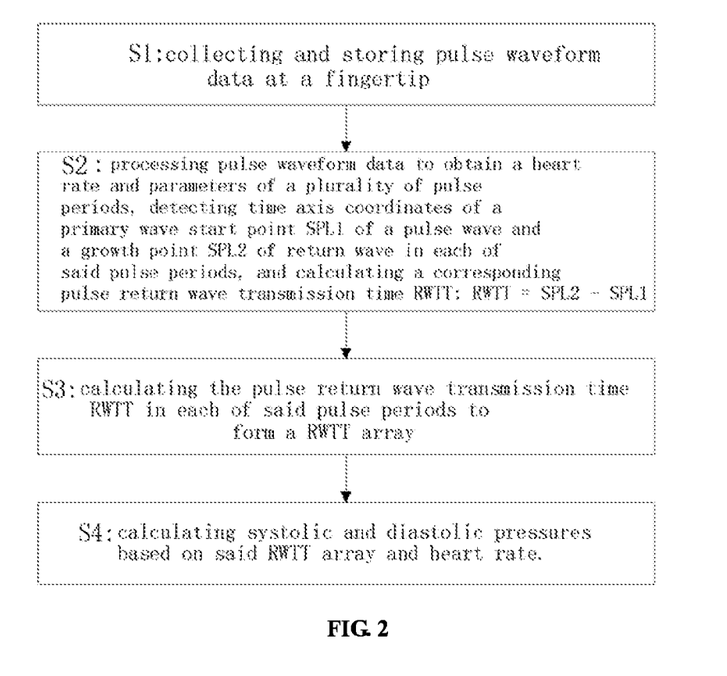
FIG. 2 is a flow chart of a blood pressure calculation method according to the present disclosure.

A blood pressure calculation method based on a pulse return wave transmission time according to the present disclosure as shown in FIG. 2 includes the following steps:

S1: collecting and storing pulse waveform data at the fingertip, wherein in the actual electronic measurement technique of the present disclosure, a blood pressure waveform at the finger is characterized by a pulse wave waveform measured thereat;

S2: processing the pulse waveform data, and deriving the heart rate and parameters of a plurality of pulse periods. Wherein, the definition of a return wave transmission time (RWTT), which is a basic key parameter for the implementation of the present disclosure, is an interval between a primary wave starting point of a blood pressure waveform and a growth point of its return wave, as shown in FIG. 1. Thus, in each of the pulse periods, by detecting the time axis coordinates of the primary wave starting point SPL1 of the pulse wave and the growth point SPL2 of return wave, a corresponding pulse return wave transmission time RWTT is calculated: RWTT=SPL2−SPL1. A difference between the definitions of RWTT and pulse wave transmission time PTT is also shown in FIG. 1, where PTT is defined as an interval between a R peak of a heart sound signal and the primary wave starting point of the blood pressure (pulse) waveform;

S3: calculating the pulse return wave transmission time RWTT in each of said pulse periods in said pulse waveform data by the above-described formula to form a RWTT array;

S4: formulas of the RWTT array and the systolic and diastolic pressures are established respectively according to the RWTT array and the heart rate, and the systolic and diastolic pressures are calculated.

The blood pressure calculation method of the disclosure uses only one sensor to measure the fingertip pulse, and is simple, convenient and quick. By analyzing the corresponding basic theory of pulse return wave and human blood pressure, the correlation models between RWTT and the systolic and diastolic pressures are established, and the systolic and diastolic pressures are calculated according to the two blood pressure models. The systolic and diastolic pressures calculated according to the present disclosure have higher accuracy, less error, and board range of application. At the same time, the disclosure perfectly combines the technique with the PPG pulse sensor, obtains the pulse waveform by making fingers contact the pulse sensor, conducts a series of analysis and calculation on the pulse waveform, and finally calculates the blood pressure and obtains the heart rate data simultaneously.

Embodiment 2

On the basis of the blood pressure calculation method based on the pulse return wave transmission time described in embodiment 1, the present disclosure further includes a step S5: correcting the finally calculated systolic and diastolic pressures for each individual, wherein a user needs to first enter the height and measurement data with standard mercury sphygmomanometer upon using the electronic product of the present disclosure, and the individual height values are used for individual blood pressure automatic correction to obtain accurate measurements.

Figure 4:
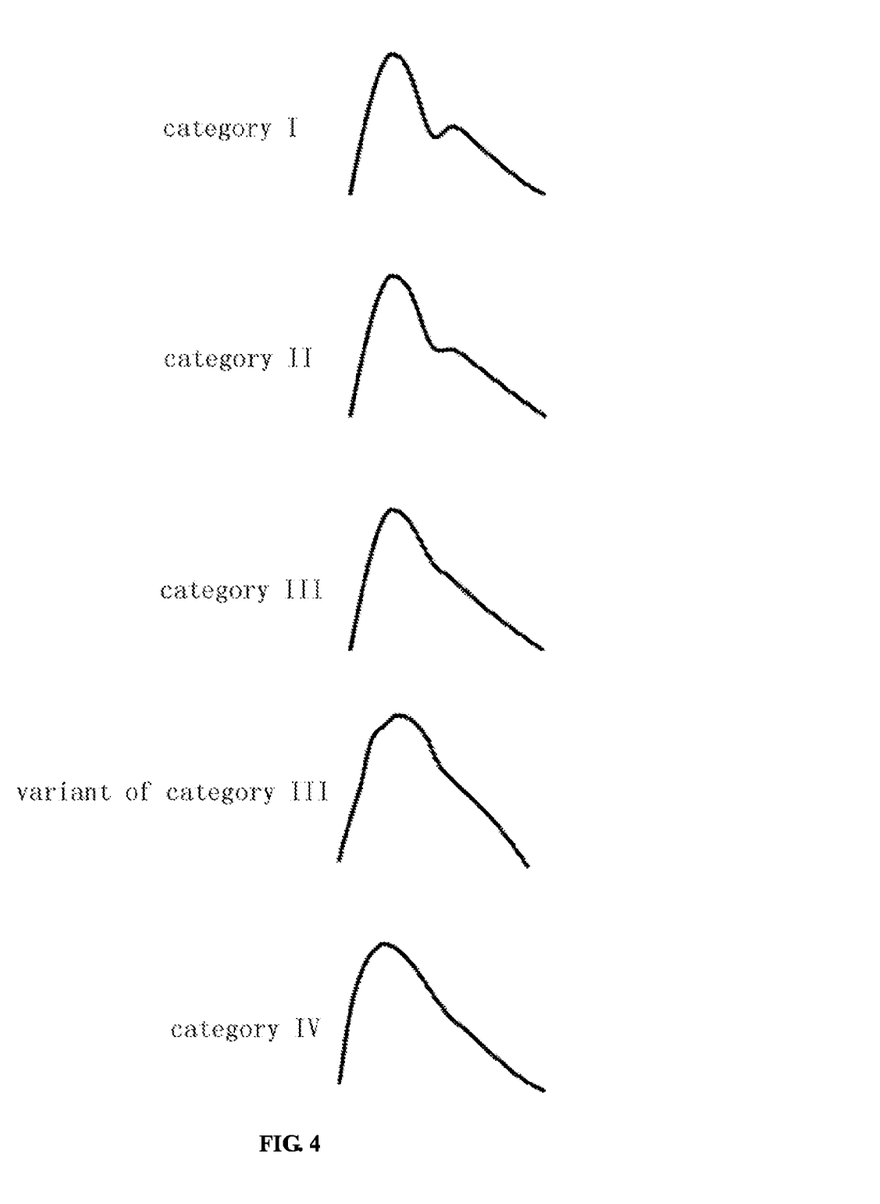
FIG. 4 shows profile plots of five types of pulse wave.

It is preferable to further include a step S21 in which said growth point SPL2 of return wave is correspondingly corrected according to the profile characteristics of different types of pulse waves. In the present embodiment, the correction of said growth point SPL2 of return wave involves five types of pulse wave profiles as shown in FIG. 4, which are divided into four categories, two of which belong to category III. For category I, there is a notch between the return wave and the primary wave. For category II, there is no notch between the return wave and the primary wave, but there is a small but rather flat transitional portion. For category III, there is no notch between the return wave and the primary wave, but a change in slope. Category III are further divided into two types, the first one with a primary peak that maintains the original shape, while the second one with a primary peak that presents an increased width and covers the corresponding part of the return wave. For category IV, the return wave portion further gets closer to and merges into the primary wave, and the change in slope between the two is not obvious. In the second-order waveform of the pulse wave of category I, the growth point SPL2 of return wave does not need to be corrected, that is, the peak position caused by the growth point of return wave. For category II and the first type of category III, the growth point SPL2 of return wave needs an appropriate fine adjustment. For the second type of category III, the growth point SPL2 of return wave needs a larger adjustment. The above mentioned adjustments are forward or backward shifting of the growth point SPL2 of return wave, which are prior art means.

Embodiment 3

On the basis of the blood pressure calculation method based on the pulse return wave transmission time described in the above embodiment 1 and embodiment 2, the systolic pressure is calculated by the following step: establishing the systolic pressure SYS formula according to said RWTT array. According to the pulse wave transmission time PTT-blood pressure BP model, a process of blood propagation from the ventricle through the artery network to the fingertip may be equivalent to a process of a pulse wave propagation in a rigid pipe, and thus the work that is done by pressure is equal to the sum of kinetic and potential energy. In case the fingers are located on the same height with the heart in the measurement, only the kinetic energy needs to be considered. According to the relevant physical theory, it may be deduced that $$SYS = K_s \cdot 266 \cdot \frac{height^2}{RWTT^2},$$

where $K_S$ is 1.5, the accuracy of which has been verified by a large number of experiments. This formula derives a systolic pressure SYS in the unit of kg/m$^3$, which may be converted into the systolic pressure in the unit of mmHg.

The diastolic pressure is defined as the lowest point of arterial blood pressure waveform when it attenuates during diastole. The rate of the attenuation of the blood pressure during diastole depends on a number of factors, including accumulation of aorta blood pressure during systole, artery system resistance (in relation to artery system, especially the stiffness of vessel wall of arteriole) and the like. Diastolic pressure is also highly correlated with BP, that is, with PTT$^2$ and RWTT$^2$. Therefore, according to the RWTT array, the first diastolic pressure DIA formula is established:

$$DIA = \frac{K_{d1}}{RWTT^2} + K_{d2} \cdot HR,$$

where $K_{d1}$ is 2.7, $K_{d2}$ is 0.5, and HR is the heart rate. This formula derives a diastolic pressure DIA in the unit of mmHg. The value of the parameters in the present disclosure may be converted according to the circumstances of use, and if the calculation formula of the present disclosure is used while just those parameters have been subjected to conventional transformation, the use shall be considered as falling into the protection scope of the present disclosure.

Embodiment 4

On the basis of the blood pressure calculation method based on the pulse return wave transmission time described in the above embodiments, the diastolic pressure is calculated as follows: according to said RWTT array, a second diastolic pressure DIA formula is established:

$$DIA = \frac{K_{d1}}{RWTT^2} + \frac{K_{d2}}{T_d} + \frac{K_{d3}}{SL},$$

where $K_{d1}$ is 2, $K_{d2}$ is 15, $K_{d3}$ is 66 ($P_{nor}$-DC), and SL is a normalized slope. This formula derives a diastolic pressure DIA in the unit of mmHg. For a particular individual, the minimum level to which the arterial blood pressure attenuates is related to the allowed attenuation time and is also related to the slope of the attenuation ramp. Wherein, the attenuation time is positively proportional to the period of the blood pressure waveform and is inversely proportional to the instantaneous heart rate. The slope of the attenuation ramp is in turn related to the strength (amplitude) of the measured pulse (blood pressure) waveform signal in the waveform, and therefore requires standardization (normalization) processing.

Figure 5:
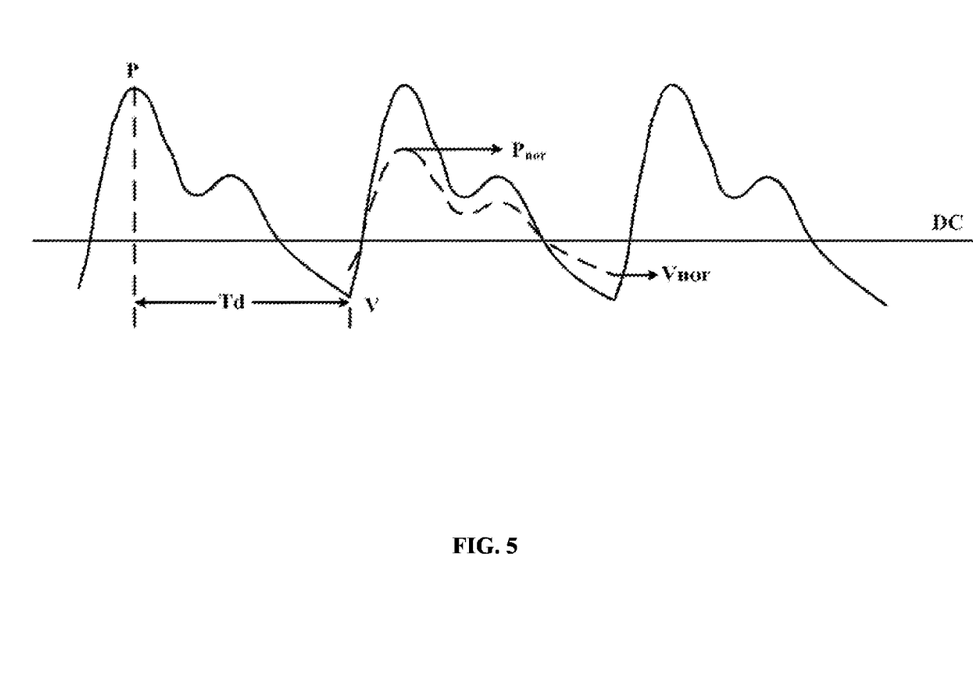
FIG. 5 shows a specific blood pressure waveform.

The schematic diagram of deriving standardized slope SL is shown in FIG. 5, where $T_d$ is the attenuation time of each waveform period, $P_{nor}$ represents the peak, and $V_{nor}$ represents the trough. Each waveform is standardized with reference to the reference peak $P_{nor}$, so that the standardized trough $V_{nor}$ is:

$$V_{nor} = DC - \frac{(DC - V)(P_{nor} - DC)}{P - DC}$$

Where DC is the amplified DC reference level of the pulse voltage waveform collected by the sensor, and the above $T_d$, $V_{nor}$, $P_{nor}$ and DC are all parameters of the pulse period, all of which are commonly used in prior art. And then the standardized slope SL of the attenuation ramp may be derived:

$$SL = \frac{P_{nor} - V_{nor}}{T_d}$$

The formula of the second diastolic pressure DIA in this embodiment is more suitable for those who have abnormal attenuation rates during blood pressure diastole, and the measured diastolic pressure is more accurate.

Embodiment 5

In the blood pressure calculation method based on the pulse return wave transmission time described in the above embodiments, the step S5 specifically includes comparing the calculated systolic and diastolic pressures with predetermined standard values. For the convenience of comparison, the calculated medians of the systolic and diastolic pressures may be used for comparison. In the comparison, for the diastolic pressure, a value obtained by subtracting the calculated value from the standard value is calculated as a diastolic pressure correction parameter $K_{dc}$, and for the systolic pressure, a value obtained by dividing the standard value by the calculated value is calculated as a systolic pressure correction parameter $K_{sc}$. Substituting said systolic pressure correction parameter $K_{sc}$ into the systolic pressure SYS formula forms a corrected systolic pressure SYS formula, and substituting the diastolic pressure correction parameter $K_{dc}$ into the first diastolic pressure DIA formula and the second diastolic pressure DIA formula forms a corrected first diastolic pressure DIA formula and a corrected second diastolic pressure DIA formula, respectively.

When a user first uses the electronic product of the present disclosure, the user may first carry on a measurement with a standard mercury sphygmomanometer and input the measurement results in advance as standard values. Then, the electronic product of the present disclosure is used to take a measurement within 5 minutes. During the calculation by the product, the systolic pressure SYS formula and the first (or second) diastolic pressure DIA formula are first used to conduct calculations, and the calculated values are compared with the standard values input by the user in advance to obtain and store permanently the values of the correction parameters $K_{sc}$ and $K_{dc}$. When the electronic product of the present disclosure is used for measurement next time, the product automatically uses the corrected systolic pressure SYS formula and the corrected first (or second) diastolic pressure DIA formula to conduct calculations. Each time the user performs the above correction process, the values of the correction parameters $K_{sc}$ and $K_{de}$ stored in the product are updated accordingly.

Said corrected systolic pressure SYS formula is, specifically, $$SYS = K_s \cdot 266 \cdot \frac{height^2}{RWTT^2} \cdot K_{sc},$$

where $K_S$ is 1.5.

The corrected first diastolic pressure DIA formula is, specifically, $$DIA = \frac{K_{d1}}{RWTT^2} + K_{d2} \cdot HR + K_{dc},$$

where $K_{d1}$ is 2.7, $K_{d2}$ is 0.5, and HR is heart rate.

The corrected second diastolic pressure DIA formula is, specifically, $$DIA = \frac{K_{d1}}{RWTT^2} + \frac{K_{d2}}{T_d} + \frac{K_{d3}}{SL} + K_{dc},$$

where $K_{d1}$ is 2, $K_{d2}$ is $K_{d3}$ is 66 ($P_{nor}$-DC), and SL is the standardized slope.

Said RWTT array in all of the above formulas can be replaced by a median RTM of the RWTT array calculated for all pulse periods collected in 10 seconds to calculate the medians of systolic and diastolic pressures over 10 seconds.

Calculating with RWTT array gives a group of data, which may be construed as real-time blood pressure data. There may be deviations between this group of data, or a certain data may have a calculation error because a certain collected waveform is not good enough. By using the median RTM, medians of the systolic and diastolic pressures within 10 seconds may be obtained, which ensures correct and stable measurement results. Said heart rate HR and standardized slope SL in all of the above formulas may be replaced by a median or average of the heart rates HR and the standardized slopes SL calculated for all pulse periods collected in 10 seconds.

The specific procedure of use of the method is provided taking a patient of the height 1.7 m as an example: before the first use of the electronic product of the present disclosure, the patient first uses a standard mercury sphygmomanometer to measure the patient's blood pressure data as follows: systolic pressure 120 mmHg, diastolic pressure 78 mmHg. The patient inputs the set of standard values into the electronic product of the present disclosure and carries on measurements with the electronic product of the present disclosure within 5 minutes. Assuming that in the first measurement, the product measures and obtains within 10 seconds a RWTT array with a median of 0.27 s, heart rates with an average of 65, $T_d$ with an average of 0.56 s, and SL with an average of 1.61 (assuming $P_{nor}$=2.6V, DC=2V, $K_{d3}$=40). Substituting these measurement data into the corrected systolic pressure SYS formula and the corrected first (or second) diastolic pressure DIA formula with a unified unit of mmHg gives:

systolic pressure SYS=118·$K_{sc}$ and first diastolic pressure DIA=69.5+$K_{dc}$ or second diastolic pressure DIA=79++$K_{dc}$.

By comparing with the standard blood pressure values, it could be obtained that $K_{sc}$=120/118=1.017, $k_{dc}$=78−69.5=8.5, or $k_{dc}$=78−79=−1. The values of the correction parameters $K_{sc}$ and $K_{dc}$ are permanently stored, and when the patient uses the electronic product of the present disclosure to perform measurements next time, the product automatically uses the corrected systolic pressure SYS formula and the corrected first (or second) diastolic pressure DIA formula to conduct calculations. Each time the patient performs the above correction process, the values of the correction parameters $K_{sc}$ and $K_{dc}$ stored in the product are updated accordingly.

For example, when the patient uses the electronic product of the present disclosure for a second time, the product measures and obtains within 10 seconds the RWTT array with a median value of 0.26 s, heart rates with an average of 70, $T_d$ with an average of 0.6 s, and SL with an average of 1.33 ($P_{nor}$, DC, $K_{d3}$ remain unchanged, since it is the same product). Substituting these measured data, as well as the stored correction parameters $K_{sc}$ and $K_{dc}$, into the corrected systolic pressure SYS formula and the corrected first (or second) diastolic pressure DIA formula gives:

systolic pressure $SYS =$ $$1.5 \times 266 \times \frac{1.7^2}{0.26^2} \times 1.017 = 17348 \text{ kg/m}^3 = 130 \text{ mmHg, and}$$

first diastolic pressure $DIA = \frac{2.7}{0.26^2} + 0.5 \times 70 + 8.5 = 83.5$ mmHg or second diastolic pressure $DIA = \frac{2}{0.26^2} + \frac{15}{0.6} + \frac{40}{1.33} - 1 = 84$ mmHg Embodiment 6

Figure 3:
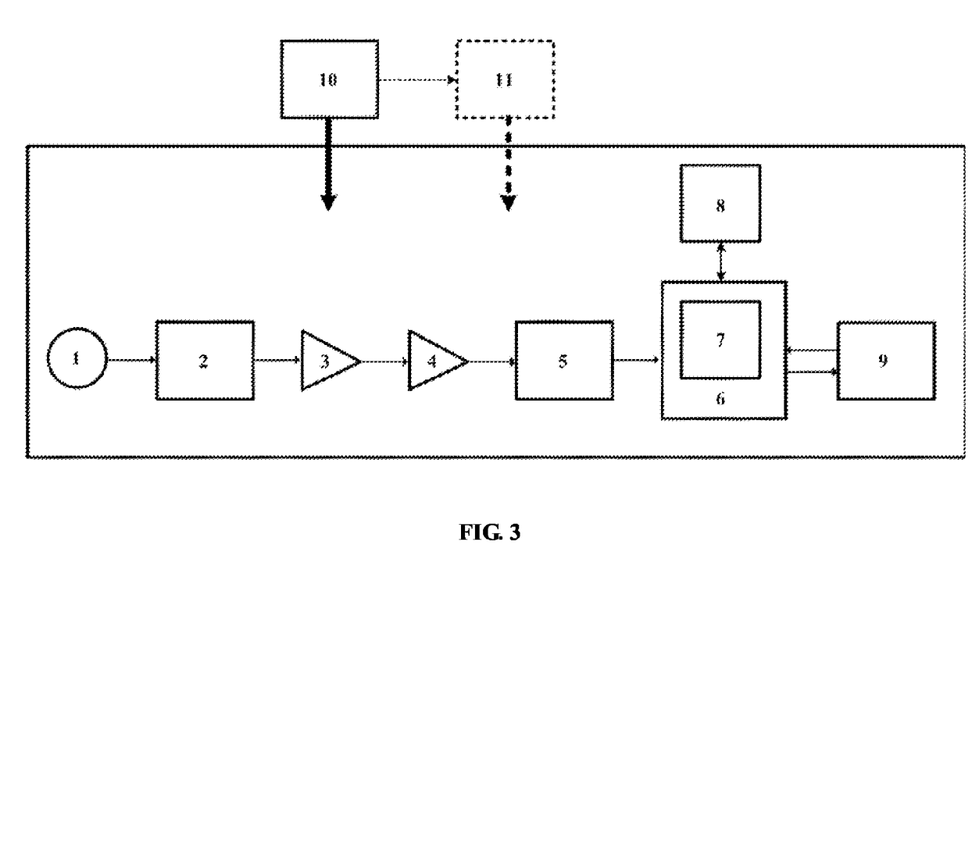
FIG. 3 is a block diagram showing the structure of a blood pressure monitor according to the present disclosure.

A blood pressure monitor based on pulse return wave transmission time, as shown in FIG. 3, includes a pulse sensor which may use a pulse sensor based on photoplethysmography that is highly sensitive and more suitable for finger contact sensing equipment.

Said pulse sensor is connected in turn to a linear current-voltage conversion circuit, a unity gain buffer, a low-pass amplifier circuit, an analog-to-digital conversion circuit and a processor. The processor is further connected with a power supply, which may use a 3.7 V (or 3.8 V) rechargeable lithium battery or nickel hydrogen battery to power the circuit, or may use a USB (5V) power supply.

The above circuits may be designed and integrated using complementary metal oxide semiconductor (CMOS) technology. CMOS technology is cheap, and has mature design and manufacturing technology, stable performance, and rapid development, and thus is preferred for large-scale integrated circuit chip standardization and miniaturization.

As other preferences, the above circuitry may also be implemented by using discrete components and integrating these discrete components on a printed circuit board. The processor may be implemented by a field programmable gate array (FPGA), or a digital signal processor (Digital Signal Processing, DSP), a microcomputer or the like.

The processor is also connected with a memory and/or display and input module and/or a low dropout linear regulator. Before the user inputs his or her own height or individual corrected blood pressure value into the input module, the system selects a default height and calculation formula to calculate blood pressure. After the user inputs his or her own height or individual corrected blood pressure value, the user's height and the calculated individual correction parameters will be permanently saved until the next new input occurs to be replaced by a new value. Said memory may be internal memory and/or external memory, specifically selected as needed, without specific limitation.

If part of the circuit requires the use of 3.3V standard voltage, it may be generated by low dropout regulator (LDO), and the corresponding signal level may be adjusted by a level shifting circuit.

The cutoff frequency of the low-pass amplifier circuit is 20-50 Hz and should not be set too low so as to avoid deformation of the original pulse waveform. In further analysis to the original pulse waveform, low frequency noise may be eliminated by the processor performing further digital filtering.

The sampling rate of said analog-to-digital conversion circuit is set to 1 kS/s, and the analog-to-digital conversion circuit should have a precision of 10 or more bits to maintain the sampling accuracy, that is, about 10,000 samples may be obtained within 10 seconds.

Said processor performs low-pass digital filtering on the digitized data with a cutoff frequency of 10 Hz to further remove the noise.

The specific way of use of the method is provided below: a pulse wave sensor 1 detects a pulse change at the finger and outputs (usually) a corresponding small current signal, and a linear current-voltage conversion circuit 2 converts the small current signal into a small voltage signal. A unity gain buffer 3 has a high input impedance which acts as a signal isolation and drives a low pass amplifier circuit 4 at next stage as a buffer. The low-pass amplifier circuit 4 amplifies the small voltage signal of the pulse to an appropriate level and performs a first low-pass filtering with a cutoff frequency of about 50 Hz to remove the high-frequency noise to a large extent without causing original pulse waveform to be deformed. An analog-to-digital conversion circuit 5 converts the analog voltage signal into a digital signal by sampling and outputs it to a processor 6. The analog-to-digital conversion circuit 5 should have a sufficiently high sampling rate to obtain a sufficient amount of original pulse wave waveform information and stops collecting after having collected a predetermined number (e.g., 10,000) of data point. The processor 6 stores the data of these original waveforms in an internal memory 7, or in an external memory 8. The processor performs the blood pressure calculation method based on the pulse return wave transmission time as described above. The processor 6 then performs in-depth processes and analysis on the data of the original waveform, finds the primary wave starting point of the pulse wave and the growth point of return wave in each pulse period according to the algorithm provided by the present disclosure, and calculates a time interval between these two as the RWTT of the period. The processor 6 hereby calculates the RWTT for all periods and takes the median RTM, and calculates the heart rate, systolic pressure, and diastolic pressure, respectively, according to the algorithm of the present disclosure.

It will be appreciated by those skilled in the art that embodiments of the present disclosure may be provided as a method, system, or computer program product. Thus, the present disclosure may take the form of a pure hardware embodiment, a pure software embodiment, or a combination of software and hardware aspects. Moreover, the present disclosure may take the form of a computer program product implemented on one or more computer usable storage media (including but not limited to disk storage, CD-ROM, optical memory, etc.) in which computer usable program code is comprised.

The present disclosure has been described with reference to a flowchart and/or block diagram of a method, apparatus (system), and computer program product according to an embodiment thereof. It will be appreciated that each process and/or block in the flowchart and/or block diagram as well as a combination of processes and/or blocks in flowcharts and/or block diagrams may be implemented by computer program instructions. These computer program instructions may be provided to a processor of a general-purpose computer, a dedicated computer, an embedded processor, or other programmable data processing apparatuses to generate a machine such that instructions executed by a processor of a computer or other programmable data processing apparatuses generate a device that implements the functions specified in one or more flows of the flowchart or one or more blocks of the block diagram.

These computer program instructions may also be stored in a computer readable memory capable of operating a computer or other programmable data processing apparatuses in a particular manner such that instructions stored in the computer readable memory produce a product that includes a command device that implements a function specified in one or more flows of the flowchart or one or more blocks of the block diagram.

These computer program instructions may also be loaded onto a computer or other programmable data processing apparatuses such that a series of operational steps are performed on the computer or other programmable apparatuses to produce computer-implemented processing, thereby instructions executed on a computer or other programmable apparatuses provide steps for implementing the functions specified in one or more flows of the flowchart or one or more blocks of the block diagram.

While the preferred embodiments of the present disclosure have been described, those skilled in the art may make further changes and modifications to these embodiments, once the basic concept of inventiveness is known. Accordingly, the appended claims are intended to be construed as including the preferred embodiments and all changes and modifications that fall within the scope of the present disclosure.

What is claimed is:

1. A method for monitoring blood pressure, performed by a processor connected to a power supply, the method comprising:

detecting, by a pulse sensor, a pulse change at a fingertip and outputting a current signal;

converting, by a linear current-voltage conversion circuit, the current signal into an analog voltage signal;

driving, by a unity gain buffer, a low-pass amplifier circuit;

amplifying and removing a high-frequency noise from the analog voltage signal, by the low-pass amplifier circuit;

converting, by an analog-to-digital conversion circuit, the analog voltage signal into a digital signal, and outputting the digital signal to the processor, as pulse waveform data;

processing, by the processor, said pulse waveform data to obtain a heart rate and parameters of a plurality of pulse periods, detecting time axis coordinates of a primary wave start point SPL1 of a pulse wave and a growth point SPL2 of a return wave in each of said plurality of pulse periods, and calculating a corresponding pulse return wave transmission time RWTT: RWTT=SPL2−SPL1;

calculating, by the processor, the pulse return wave transmission time RWTT in each of said pulse periods to form a RWTT array; and calculating, by the processor, systolic and diastolic pressures based on said RWTT array and the heart rate.

2. The method according to claim 1, further comprising correcting said growth point SPL2 of the return wave in accordance with profile characteristics of different types of pulse waves.

3. The method according to claim 1, wherein the calculating of the systolic pressure comprises establishing a systolic pressure SYS formula according to said RWTT array $$SYS = K_s \cdot 266 \cdot \frac{height^2}{RWTT^2},$$

where $K_S$ is 1.2-1.8, and the height is a user's height.

4. The method according to claim 1, wherein the calculating of the diastolic pressure comprises establishing a first diastolic blood pressure DIA formula according to said RWTT array $$DIA = \frac{K_{d1}}{RWTT^2} + K_{d2} \cdot HR,$$

where $K_{d1}$ is 2.1-3.3, $K_{d2}$ is 0.3-0.8, and HR is the heart rate.

5. The method according to claim 1, wherein the calculating of the diastolic pressure comprises establishing a second diastolic blood pressure DIA formula according to said RWTT array $$DIA = \frac{K_{d1}}{RWTT^2} + \frac{K_{d2}}{T_d} + \frac{K_{d3}}{SL},$$

where $K_{d1}$ is 1.6-2.4, $K_{d2}$ is 12-18, $K_{d3}$ is 52 ($P_{nor}$-DC) to 79 ($P_{nor}$-DC), SL is a normalized slope, $T_d$ is a length of diastole in the pulse period, and $P_{nor}$ and DC are reference peak and reference DC voltage in the pulse period, respectively.

6. The method according to claim 3, further comprising correcting the calculated systolic pressure for each individual,
wherein the correcting comprises:
comparing the calculated systolic pressure with a predetermined standard value, and obtaining a systolic pressure correction parameter $K_{sc}$; and
substituting the systolic pressure correction parameter $K_{sc}$ into the systolic pressure SYS formula to form a corrected systolic pressure SYS formula,
wherein the corrected systolic pressure SYS formula is $$SYS = K_s \cdot 266 \cdot \frac{height^2}{RWTT^2} \cdot K_{sc},$$

where $K_S$ is 1.2-1.8, $K_{sc}$ is the systolic pressure correction parameter, and the height is a user's height.

7. The method according to claim 4, further comprising correcting the calculated diastolic pressure for each individual,
wherein the correcting comprises:
comparing the calculated diastolic pressure with a predetermined standard value, and obtaining a diastolic pressure correction parameter $K_{dc}$; and
substituting the diastolic pressure correction parameter $K_{dc}$ into the first diastolic blood pressure DIA formula, to form a corrected first diastolic blood pressure DIA formula,
wherein the corrected first diastolic blood pressure DIA formula is $$DIA = \frac{K_{d1}}{RWTT^2} + K_{d2} \cdot HR + K_{dc},$$

where $K_{d1}$ is 2.1-3.3, $K_{d2}$ is 0.3-0.8, HR is the heart rate, and $K_{dc}$ is the diastolic pressure correction parameter.

8. The method according to claim 5, further comprising correcting the calculated diastolic pressure for each individual,
wherein the correcting comprises:
comparing the calculated diastolic pressure with a predetermined standard value, and obtaining a diastolic pressure correction parameter $K_{dc}$; and
substituting the diastolic pressure correction parameter $K_{dc}$ into the second diastolic blood pressure DIA formula, to form a corrected second diastolic blood pressure DIA formula,
wherein the corrected second diastolic blood pressure DIA formula is $$DIA = \frac{K_{d1}}{RWTT^2} + \frac{K_{d2}}{T_d} + \frac{K_{d3}}{SL} + K_{dc},$$

where $K_{d1}$ is 1.6-2.4, $K_{d2}$ is 12-18, $K_{d3}$ is 52 ($P_{nor}$-DC) to 79 ($P_{nor}$-DC), SL is the normalized slope, $K_{dc}$ is the diastolic pressure correction parameter, and $T_d$ is the length of diastole in the pulse period.

9. The method according to claim 6, wherein the predetermined standard value comprises a systolic pressure measured with a standard mercury sphygmomanometer, and
the systolic pressure correction parameter $K_{sc}$ is obtained by dividing the systolic pressure measured with the standard mercury sphygmomanometer by the systolic pressure calculated by the systolic pressure SYS formula.

10. The method according to claim 7, wherein the predetermined standard value comprises a diastolic pressure measured with a standard mercury sphygmomanometer, and
the diastolic pressure correction parameter $K_{dc}$ is obtained by subtracting the diastolic pressure calculated by the first diastolic blood pressure DIA formula from the diastolic pressure measured with the standard mercury sphygmomanometer.

11. The method according to claim 8, wherein the predetermined standard value comprises a diastolic pressure measured with a standard mercury sphygmomanometer, and
the diastolic pressure correction parameter $K_{dc}$ is obtained by subtracting the diastolic pressure calculated by the second diastolic blood pressure DIA formula from the diastolic pressure measured with the standard mercury sphygmomanometer.

12. A method for monitoring blood pressure, performed by a processor connected to a power supply, the method comprising:
detecting, by a pulse sensor, a pulse change at a fingertip and outputting a current signal;
converting, by a linear current-voltage conversion circuit, the current signal into an analog voltage signal;
driving, by a unity gain buffer, a low-pass amplifier circuit;
amplifying and removing a high-frequency noise from the analog voltage signal, by the low-pass amplifier circuit;
converting, by an analog-to-digital conversion circuit, the analog voltage signal into a digital signal, and outputting the digital signal to the processor, as pulse waveform data;
processing, by the processor, said pulse waveform data to obtain a heart rate and parameters of a plurality of pulse periods, detecting time axis coordinates of a primary wave start point SPL1 of a pulse wave and a growth point SPL2 of a return wave in each of said plurality of pulse periods, and calculating a corresponding pulse return wave transmission time RWTT: RWTT=SPL2−SPL1;
calculating, by the processor, the pulse return wave transmission time RWTT in each of said pulse periods to form a RWTT array;
calculating a median of the calculated RWTT array for all of the pulse periods collected in a predetermined time period; and
calculating medians of systolic and diastolic pressures over the predetermined time period based on the calculated median of the RWTT array and the heart rate.

13. The method according to claim 4, wherein median or average of the calculated heart rate HR for all of the pulse periods collected in 10 seconds is used as said heart rate HR.

14. The method according to claim 5, wherein median or average of the calculated normalized slope SL for all of the pulse periods collected in 10 seconds is used as said normalized slope SL.

15. A blood pressure monitor for monitoring blood pressure, comprising:
- a pulse sensor configured to collect pulse waveform data at a fingertip; and
- a processor configured to receive said pulse waveform data collected by the pulse sensor, process said pulse waveform data to obtain a heart rate and parameters of a plurality of pulse periods, detect time axis coordinates of a primary wave start point SPL1 of a pulse wave and a growth point SPL2 of a return wave in each of said plurality of pulse periods, and calculate a pulse return wave transmission time RWTT: RWTT=SPL2−SPL1 in each of said pulse periods to form a RWTT array, calculate systolic and diastolic pressures based on said RWTT array and the heart rate,
- wherein a linear current-to-voltage conversion circuit, a unity gain buffer, a low-pass amplifier circuit, an analog-to-digital conversion circuit are connected between the pulse sensor and the processor, and the processor is further connected with a power supply.

16. The blood pressure monitor according to claim 15, wherein only one said pulse sensor is provided, and said processor is further connected with a memory and/or a display and input module and/or a low dropout linear regulator.

17. The blood pressure monitor according to claim 15, wherein the low-pass amplifier circuit has a cutoff frequency of 20-50 Hz.

18. The blood pressure monitor according to claim 15, wherein the analog-to-digital conversion circuit has its sampling rate set to 1 kS/s.

19. The blood pressure monitor according to claim 15, wherein the processor performs low pass digital filtering on digitized data with a cutoff frequency of 10 Hz to further remove the noise.

20. The method for monitoring blood pressure according to claim 1, further comprising:
- receiving, by the processor, a height of a person having the fingertip,
- wherein, in the calculating of the systolic and diastolic pressures, the systolic pressure is calculated based on the received height.

* * * * *